(12) United States Patent
Riecke

(10) Patent No.: US 8,146,593 B2
(45) Date of Patent: Apr. 3, 2012

(54) PROCESS AND DEVICE FOR SEPARATING CARBON DIOXIDE FROM A BREATHING GAS MIXTURE BY MEANS OF A FIXED SITE CARRIER MEMBRANE

(75) Inventor: Michael Riecke, Luebeck (DE)

(73) Assignee: Dräger Medical GmbH, Lübeck (DE)

( * ) Notice: Subject to any disclaimer, the term of this patent is extended or adjusted under 35 U.S.C. 154(b) by 1131 days.

(21) Appl. No.: 11/850,944

(22) Filed: Sep. 6, 2007

(65) Prior Publication Data

US 2008/0060651 A1 Mar. 13, 2008

(30) Foreign Application Priority Data

Sep. 8, 2006 (DE) .......................... 10 2006 042 348

(51) Int. Cl.
*A62B 19/00* (2006.01)
(52) U.S. Cl. ......... 128/205.28; 128/205.12; 128/205.27; 128/204.18; 128/910; 128/914
(58) Field of Classification Search ............. 128/205.27, 128/203.12, 204.18, 205.12, 205.28, 910, 128/914
See application file for complete search history.

(56) References Cited

U.S. PATENT DOCUMENTS

| 4,909,989 | A | * | 3/1990 | Fukazawa et al. | ............... | 422/48 |
| 5,131,927 | A | | 7/1992 | Bikson et al. | | |
| 2004/0187871 | A1 | * | 9/2004 | Kimmel et al. | .......... | 128/204.23 |
| 2006/0090644 | A1 | * | 5/2006 | Sirkar | ................ | 95/45 |

FOREIGN PATENT DOCUMENTS

| DE | 2 140 902 | | 3/1973 |
| DE | 696 19 377 | T2 | 7/2002 |
| DE | 102004052755 | B3 * | 11/2005 |
| EP | 1 803 479 | A1 | 7/2007 |
| WO | WO 97/03118 | A1 | 1/1997 |
| WO | WO 2004/050154 | A1 | 6/2004 |
| WO | WO 2005/089907 | | 9/2005 |
| WO | WO 2005089907 | A1 * | 9/2005 |

OTHER PUBLICATIONS

Taek-Joong Kim, Baon Li, May-Britt Haegg; Novel Fixed-Site-Carrier Polyvinylamine Membrane for Carbon Dioxide Capture; Journal of Polymer Science; Part B: Polymer Physics, vol. 42, 4326-4336 (2004).

* cited by examiner

*Primary Examiner* — Clinton T Ostrup
(74) *Attorney, Agent, or Firm* — McGlew and Tuttle, P.C.

(57) ABSTRACT

A process and a device are provided for separating carbon dioxide from a breathing gas mixture by means of a "Fixed Site Carrier" membrane. The breathing gas mixture is guided in the device on a side of a selective, semipermeable membrane, which is provided with amine groups, which are bound covalently to a polymer. Through the membrane, the transport of the components of the gas mixture can take place. The membrane is selected to be such that the permeability for $CO_2$ is substantially higher than the permeability for the other gas components of the breathing gas mixture. The membrane has or is associated with means for guiding the gas, which acts to guide the gas mixture on one side along the membrane. The membrane separates volume areas in which different $CO_2$ partial pressures prevail from one another.

28 Claims, 2 Drawing Sheets

US 8,146,593 B2

PROCESS AND DEVICE FOR SEPARATING CARBON DIOXIDE FROM A BREATHING GAS MIXTURE BY MEANS OF A FIXED SITE CARRIER MEMBRANE

CROSS REFERENCE TO RELATED APPLICATIONS

This application claims the benefit of priority under 35 U.S.C. §119 of German Patent Application DE 10 2006 042 348.8 filed Sep. 8, 2006, the entire contents of which are incorporated herein by reference.

FIELD OF THE INVENTION

The present invention pertains to a process and a device for separating carbon dioxide ($CO_2$) from an expiratory breathing gas mixture. The separation takes place by means of a membrane.

BACKGROUND OF THE INVENTION

A semipermeable membrane, with which separation of $CO_2$ is possible, is described in WO 2005/089907 A1 and the publication "Novel Fixed-Site-Carrier Polyvinylamine Membrane for Carbon Dioxide Capture," T.-J. Kim, B. Li, M. B. Hägg, Journal of Polymer Science; Part B: Polymer Physics, Vol. 42, 4326-4336 (2004).

The separation of $CO_2$ from carbon dioxide-containing gas mixtures, which contain halogenated hydrocarbons, as they occur above all in the field of medicine, in which artificial respiration is combined with the administration of gaseous anesthetics, is a technically demanding task.

It has been known for a long time in various respiration processes that the breathing gases administered are prepared in a cyclic process for reasons of economy, safety and environmental protection, and components being consumed are replaced by supplementary feed and components whose concentration increases are maintained below a critical concentration value by separation.

The most important component whose concentration increases in a respiration system is carbon dioxide. An increase in the carbon dioxide concentration in respiration systems, as a result of which concentration values of half of one percent would be exceeded, is generally to be avoided. The breathing in of carbon dioxide at concentrations of 0.5% may already cause headache and increase the respiratory stimulus, and it displaces other gases that are necessary for the supply of a patient.

The percentage of carbon dioxide that is to be removed depends on the particular application. Expiratory breathing air contains approximately 5% carbon dioxide. This concentration is to be reduced in cyclic processes to a maximum of 0.5%. In closed breathing circuits, as they occur in space applications or in mining, the percentage of carbon dioxide is usually to be reduced to markedly lower concentrations. The gas mixture from which the carbon dioxide is to be removed is likewise subject to variations in terms of its composition from one application to the next.

In medical applications, the breathing gas mixture frequently contains nitrous oxide, xenon, helium as well as volatile anesthetics and a number of trace gases that are present because of physiological reasons, such as methane or acetone, besides the components of the air, namely, nitrogen, oxygen, argon and water. The volatile gaseous anesthetics are usually halogenated hydrocarbons.

It is known that carbon dioxide can be bound to adsorbing substances in cyclic processes. These substances are based, as a rule, on hydroxides, for example, calcium hydroxide, sodium hydroxide and potassium hydroxide or mixtures of these components, which are frequently called "breathing lime." These components have a number of drawbacks. Soda lime is not reusable. Lime cartridges packaged in the usual manner therefore have a limited capacity and are to be replaced cyclically as a function of this capacity. Soda lime is corrosive in a moist environment, and special measures must therefore be taken for effective protection against the dust. The effectiveness of absorption declines when the lime dries out. The state of saturation of a lime filling cannot be displayed reliably with sufficient certainty. Moreover, lime cartridges offer a considerable and possibly variable flow resistance to the breathing gas flow, which may lead to a marked loss of comfort in cyclic systems with lime-based absorption. The absorption reaction leads to a considerable release of heat of reaction under special conditions, which may bring about a cracking reaction in the presence of halogenated hydrocarbons, as a result of which toxic fractions of these substances may possibly be released.

Furthermore, it is known that the separation of carbon dioxide from a gas mixture can be carried out by guiding the gas mixture past a semipermeable membrane (DE 21 40 902). However, prior-art semipermeable membranes have insufficient selectivity in mixtures that contain carbon dioxide and nitrogen, carbon dioxide and nitrous oxide or carbon dioxide and halogenated hydrocarbons, or they are characterized by variable selectivity, which may be affected by swelling effects or a strong moisture dependence, so that use for patient- and safety-relevant applications is not considered. Another drawback of conventional semipermeable membranes is their lack of stability against halogenated hydrocarbons, which makes them unsuitable for long-term applications, in which permanent or varying exposure to halogenated hydrocarbons is to be expected.

Other prior-art processes, which are based on the use of liquid sorbents such as primary, secondary or tertiary amines in a solution, for example, methanolamine or mixtures thereof, are not considered for application in respiration systems because the processes are either technically or chemically too complicated and hence expensive or they are to be ruled out because of an excessively high vapor pressure of the sorbent, because they could thus give rise to toxic concentrations in the area in which the breathing gas is guided.

SUMMARY OF THE INVENTION

The object of the present invention is to provide a process and a device for separating carbon dioxide from breathing gas mixtures, which are characterized, besides by safe use and inexpensive implementation, by high selectivity of $CO_2$ separation from expiratory breathing gas mixtures.

According to the invention, a process is provided for separating $CO_2$ from a breathing gas mixture. The process comprises providing a selective and semipermeable membrane which is provided with amine groups bound covalently to a polymer. A breathing gas mixture is guided on one side of the selective and semipermeable membrane such that transport of the components of the gas mixture takes place through the selective and semipermeable membrane.

According to another aspect of the invention, a device is provided for separating $CO_2$ from a breathing gas mixture. The device comprises a breathing gas mixture flow space through which a breathing gas mixture flows and another gas flow space. A separating element comprising a selective semipermeable membrane separates volume areas of the breathing gas mixture flow space and the another gas flow space on each side of the selective semipermeable membrane. The selective semipermeable membrane defines a breathing gas mixture guide on one side of the selective semipermeable membrane for forming a separating element. The selective semipermeable membrane comprises amine groups bound covalently to a polymer, through which transport of the components of the gas mixture can take place. The selective semipermeable membrane has a permeability for $CO_2$ that is substantially higher than the permeability for the other gas components of the breathing gas mixture. The selective semipermeable membrane guides the gas mixture along the membrane to separate the volume areas on each side of the selective semipermeable membrane in which different $CO_2$ partial pressures prevail from one another.

It was determined that effective separation of $CO_2$ from the breathing gas mixture can be carried out by means of the so-called "fixed site carrier membranes" (FSC).

Since the membrane area necessary for the separation task shall be kept small for cost reasons, the thickness of the selective, semipermeable layer of the membrane is of great significance. In case of layer thicknesses below 100 μm, it is recommended that the selective layer be selected as a layer with a porous support structure with the highest possible permeability, suitable support function, chemical resistance and small-cell structure on at least one side. This is achieved with an asymmetrical hollow fiber membrane made, for example, of polysulfone, polyacrylonitrile, cellulose acetate or polyether sulfone. The mechanical structure of such a support structure is especially such that the pore diameter decreases greatly from one side of the membrane to the other, so that a thin selective layer of a maximum thickness of 100 μm can be applied to this side of the minimum pore size. Larger pores are to be selected towards the other side in order to increase the diffusion properties.

To attain the selectivity of the membrane, a dense, possibly thin, selective layer must be applied to the porous support structure. This is carried out by means of casting or coating technologies. So-called dipcoating processes are especially suitable because of their high throughput capacity in the production. The selective layer has various functions. It must have high permeability for $CO_2$ and sufficient selectivity for the other gases used. The high selectivity of the selective layer of the membrane is achieved by crosslinked polymers with free amine groups.

The overall structure of the membrane (support structure plus selective semipermeable layer) must be chemically resistant to the gases and vapors being used. The materials used are to be selected for hygienic reasons to be such that the entire membrane module used can be cleaned or, better yet, sterilized. For reasons of practicality, steam sterilization is to be preferred here. This means a necessary temperature resistance of 135° C. of the materials used. Furthermore, the structure must be mechanically stable. This means that the membrane must not lose its properties during handling and usual gas admission variants.

Such selective, semipermeable membranes have an extremely high selectivity for carbon dioxide against nitrous oxide, oxygen, nitrogen, xenon or halogenated hydrocarbons. However, these membranes have an extraordinarily low transport capacity for $CO_2$ under dry ambient conditions, which would lead to an unacceptable area requirement for the selective permeable membrane for the separation of $CO_2$ from the breathing gas.

It was surprisingly found that when the membranes being considered are specifically exposed to the expired breathing gas mixture on at least one side, their selectivity for the transport of carbon dioxide declines only marginally, but the transport capacity or effective permeability for carbon dioxide increases rapidly.

The present invention consists of a process and a device for the separation of $CO_2$ from a breathing gas mixture, in which process the breathing gas mixture is led along one side of a special semipermeable membrane, through which transport of the components of the gas mixture can take place, the carriers in the membrane being selected to be such that the transport of $CO_2$ takes place substantially more effectively than the transport of the other gas components of the breathing gas mixture.

The membranes used according to the present invention consist of a porous polymer carrier as a support structure, on the surface of which a dense, selective, semipermeable membrane, which brings about an especially effective carbon dioxide transport at high selectivity, is fixed on one side. The transport mechanism of $CO_2$ in the selective membrane is based on the reversible formation of $HCO_3$ from $CO_2$ and $H_2O$ on an amine group. This amine group is firmly bound to a polymer.

The necessary moisture is provided by the expiratory breathing air. An additional humidifier may be advantageous if so much moisture is extracted from the gas mixture during the separation for technological reasons that conditions that lead to drying out of the membrane, which compromises the transport capacity, would become established in the vicinity of the membrane without additional humidification.

It becomes possible to carry out the process according to the present invention especially effectively if a $CO_2$ partial pressure that is below 500 Pa is set on the side of the membrane facing away from the breathing gas mixture. This can be advantageously achieved by flushing with gas on the side of the membrane facing away from the breathing gas mixture. Rapid removal of the separated carbon dioxide is thus always ensured. In another advantageous variant of the process according to the present invention, the lowering of the $CO_2$ partial pressure is brought about by lowering the overall pressure on the side of the membrane facing away from the breathing gas mixture. A volume area that is limited at least partially by the membrane and is located on the side of the membrane facing away from the breathing gas mixture is evacuated for this purpose. The evacuation is performed with usual vacuum technological means.

It is especially advantageous if a plurality of methods for reducing the $CO_2$ partial pressure are combined with one another, i.e., the setting of the $CO_2$ partial pressure by flushing with gas on the side of the membrane facing away from the breathing gas mixture and by lowering the overall pressure on the side of the membrane facing away from the breathing gas mixture.

An essential advantage of the membranes used is especially that they have high resistance to halogenated hydrocarbons. They are therefore especially suitable for long-term applications in anesthesia and respiration systems, in which an appreciable exposure to these substances is to be expected.

In case of the separation of carbon dioxide from breathing gas mixtures that contain halogenated hydrocarbons, it is advantageous to select the membrane to be such that the transport of $CO_2$ takes place with a selectivity of at least 50 relative to the transport of halogenated hydrocarbons.

The selective layer of the membrane consists of polyvinylamine in an advantageous embodiment. The membrane consists in its parts of nontoxic materials, which develop a partial pressure of less than 1,000 Pascal under the conditions prevailing in anesthesia or respiration systems, or whose partial pressure remains below a limit value, e.g., a threshold limit value. The membranes advantageously have the property of not dissolving more than 10 wt. % of a halogenated hydrocarbon.

A species that transports $CO_2$ especially effectively in combination with moisture and is responsible for the high carbon dioxide selectivity preferably consists of polyvinylamine.

It is especially advantageous if the selective layer of the membrane is in an alkaline medium. This can be achieved by corresponding pH buffer systems being dissolved in the membrane.

It is indispensable that the selective membrane layer contain components that have functional groups, via which selective transport of carbon dioxide can take place. These include primary, secondary and tertiary amines. It is necessary for an effective separation process to expose at least one side of the membrane according to the present invention to an environment that contains a relative humidity above 60%. Expiratory breathing gases are especially well suited for moistening the membrane, because they are characterized by 100% relative humidity at 37° C.

Devices for carrying out the process according to the present invention have as the separating element at least one selective, semipermeable membrane, through which transport of the components of the breathing gas mixture can take place, the selective layer being selected to be such that the transport of $CO_2$ takes place substantially more effectively than the transport of the other gas components of the breathing gas mixture. Furthermore, means for guiding the gas are available, which guide the breathing gas mixture along the membrane on one side, the membrane separating volume areas in which different $CO_2$ partial pressures prevail.

Usual breathing gas systems have a strong condensation from the expiration moisture, because the breathing gas has a relative humidity of 100% at 37° C., but usual working environments are below 37° C. This condensation in the breathing cycles is undesirable. A method to prevent the condensation is to maintain the breathing gas system, as well as the membrane module, above the current dew point. This can be brought about by means of an auxiliary heater or by the use of the waste heat of the device.

The separation unit is advantageously configured in the form of a counterflow membrane module and integrated in a respirator or anesthesia apparatus. In a special embodiment, the membrane is equipped with a selective layer, which brings about the transport of water to the side of the porous membrane facing away from the breathing gas mixture, besides an effective transport of $CO_2$. Condensation within the breathing gas guide is counteracted in this manner. At the same time, the moisture is utilized to make possible a better $CO_2$ transport through the membrane.

The present invention will be explained in more detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENTS

Figure 1:
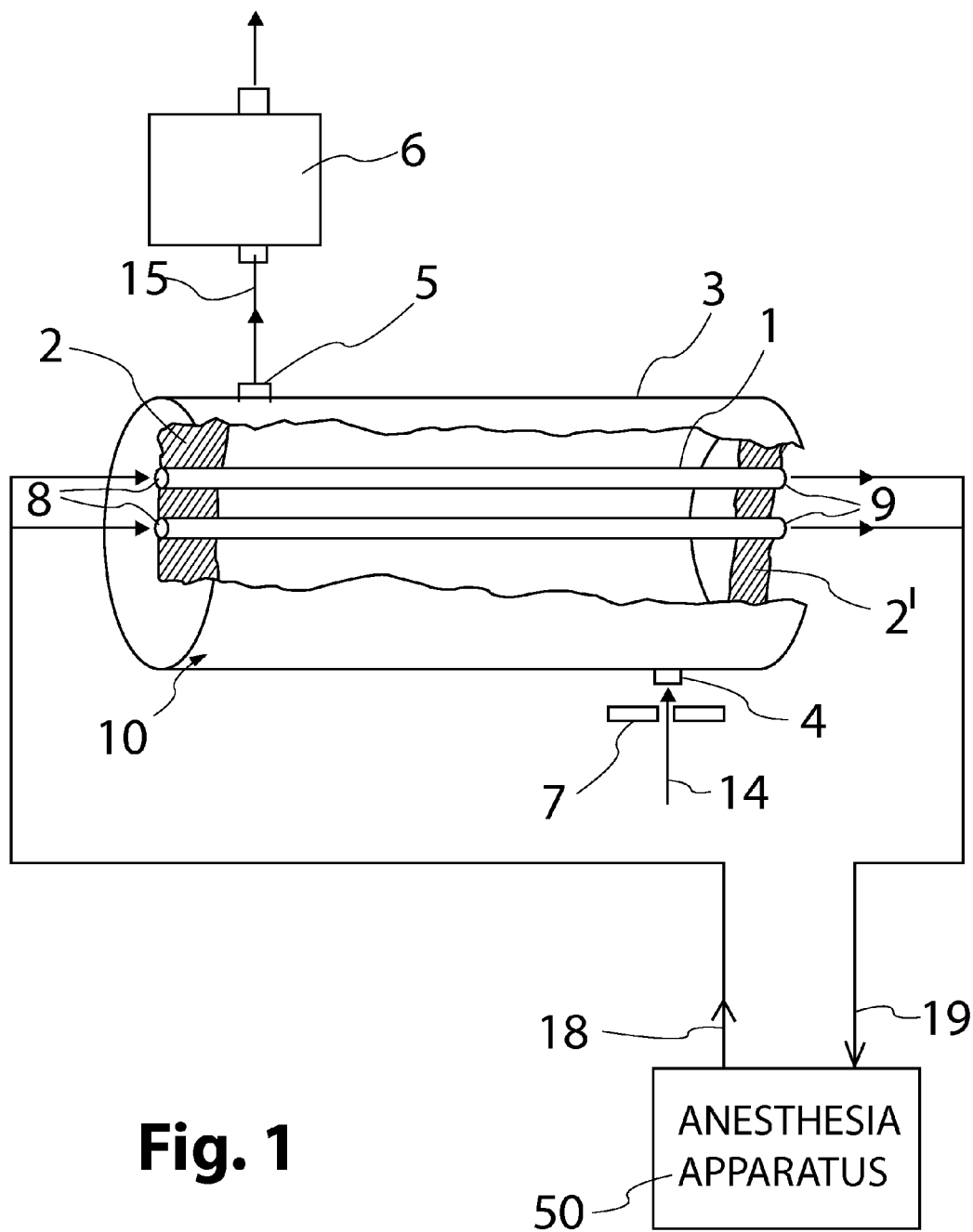
FIG. 1 is a schematic view showing a counterflow hollow fiber membrane module for carrying out the process according to the present invention.

Referring to the drawings in particular, FIG. 1 shows a counterflow hollow fiber membrane module, with hollow fibers 1, integrated in the expiratory branch of the breathing gas guide as a separating element for separating carbon dioxide from the expiratory breathing gas mixture, which may contain, among other things, halogenated hydrocarbons. This counterflow hollow fiber membrane module has a number of hollow fibers 1 extending in parallel, whose walls are formed by a selective, semipermeable membrane. The positions of the hollow fibers 1 extending in parallel are stabilized by their ends being molded in a common molding 2, 2'. The openings of the hollow fibers 1 remain non-closed. The entire module is shaped in the form of a cylinder, whose jacket surface is formed by a gas-impermeable wall 3. The moldings 2, 2' are sealingly connected to the gas-impermeable wall 3. The hollow fibers 1 extending in parallel pass through the interior of the cylinder, and gas transport between the interior of the hollow fibers 1 and the intermediate space between the hollow fibers 1 is possible only through the membrane. The interior space of the cylinder represents a volume area that is at least partially limited by the membrane. Two openings 4, 5, one of which can be used as an inlet opening 4 and the other as an outlet opening 5, pass through the jacket surface of the cylinder.

Flow can pass through the counterflow hollow fiber membrane module in two paths. The first path, with branches 18 and 19, passes through the hollow fibers 1 arranged in parallel, and the second path, with branches 14 and 15, passes through the openings 4, 5 in the jacket surface of the cylinder. The two flow paths are separated from one another by the membrane of the walls of the hollow fibers 1 only. If gas mixtures that differ in terms of their $CO_2$ partial pressures flow through the flow paths, the $CO_2$ passes through into the volume with the lower $CO_2$ partial pressure due to the selective permeability. The direction of the partial pressure gradient makes, in principle, no difference for the mode of action according to the present invention. The flow path 18, 19 through the hollow fibers 1 is integrated into the expiratory branch of the breathing gas guide of the anesthesia apparatus 50 in this example. The second flow path 14, 15 is used for passing through air as the flushing gas. It is guaranteed hereby that carbon dioxide, whose concentration is increasing, is flushed rapidly out of the intermediate space between the hollow fibers 1, as a result of which a $CO_2$ partial pressure that corresponds to the ambient air will always approximately prevail on the side of the selective permeable membrane facing away from the breathing gas mixture.

A further increase in the performance capacity of the process according to the present invention can be achieved if the outlet opening 5 is connected to a vacuum pump 6, which lowers the overall pressure in the intermediate space between the hollow fibers 1 and if air is admitted as a flushing gas optionally through a pneumatic throttle 7.

The openings 8 of the hollow fibers 1 on the left-hand side of the module form the breathing gas inlet. The openings 9 of the hollow fibers 1 on the right-hand side of the module form the breathing gas outlet.

In a preferred embodiment, the counterflow hollow fiber membrane module acting as a $CO_2$-separating element is equipped with a memory element 10, which is designed especially as a transponder, can be read in a wireless manner and contains a model identification and/or operating parameters and/or characteristics of the element for identification and/or calculation of the state of consumption or the remaining use time of the element. The evaluation or calculation is carried out especially in a computing unit of the anesthesia apparatus or respirator, which uses the separating element.

Figure 2:
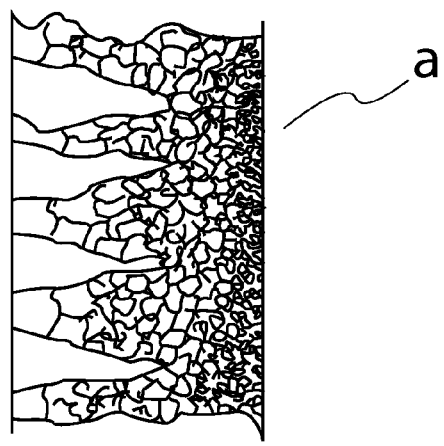
FIG. 2 is a schematic view showing the overall design of the selective, semipermeable membrane with the asymmetrical support structure with the larger pores on the left-hand side of FIG. 2 and with the selective, semipermeable layer applied, designated by "a," on the right-hand side on the support structure.

FIG. 2 shows the design of the semipermeable membrane. The pore structure is such that the pore diameter decreases from one side of the membrane to the other.

While specific embodiments of the invention have been shown and described in detail to illustrate the application of the principles of the invention, it will be understood that the invention may be embodied otherwise without departing from such principles.

What is claimed is:

1. A process for separating carbon dioxide ($CO_2$) from a breathing gas mixture, the process comprising:
providing a breathing gas device which provides an expired breathing gas mixture flow;
providing a breathing gas mixture flow space through which the expired breathing gas mixture flows;
providing another gas flow space;
providing a separating element comprising a selective semipermeable membrane separating volume areas of said breathing gas mixture flow space and said another gas flow space on each side of said selective semipermeable membrane, said selective semipermeable membrane defining a breathing gas mixture guide on one side of said selective semipermeable membrane for forming a separating element, said selective semipermeable membrane comprising a porous polymer support structure and amine groups bound covalently to the polymer, through which transport of the components of the gas mixture can take place, said selective semipermeable membrane having a permeability for $CO_2$ that is substantially higher than the permeability for the other gas components of the breathing gas mixture, said selective semipermeable membrane guiding the gas mixture along the membrane to separate said volume areas on each side of said selective semipermeable membrane;
providing a means for reducing $CO_2$ partial pressure in said another gas flow space such that a $CO_2$ partial pressure in said another gas flow space is below a $CO_2$ partial pressure prevailing in said breathing gas mixture flow space;
guiding the expired breathing gas mixture on one side of the selective and semipermeable membrane such that transport of the components of the gas mixture takes place through the selective and semipermeable membrane.

2. A process in accordance with claim 1, wherein the breathing gas mixture contains halogenated hydrocarbons and transport of the components of the gas mixture results in a separation of $CO_2$ from the breathing gas mixture.

3. A process in accordance with claim 2, wherein the transport of $CO_2$ takes place with a selectivity of at least 50 relative to the transport of halogenated hydrocarbons.

4. A process in accordance with claim 1, wherein the breathing gas mixture is guided along one side and said means for reducing $CO_2$ partial pressure continuously supplies air, guided as a flushing gas, on the other side of the membrane under substantially equal overall pressure, the membrane having a selectivity of at least 500 for $CO_2$ relative to $N_2$.

5. A process in accordance with claim 1, wherein said means for reducing $CO_2$ partial pressure establishes a pressure below 500 Pa on the side of the membrane facing away from the breathing gas mixture.

6. A process in accordance with claim 5, wherein said means for reducing $CO_2$ partial pressure comprises a gas flushing means provided in communication with said another gas flow space for continuously moving flushing gas through said another gas flow space to set the partial pressures of $N_2$, $CO_2$ and $H_2O$ by the flushing gas on a side of the membrane facing away from the breathing gas mixture.

7. A process in accordance with claim 5, wherein said means for reducing $CO_2$ partial pressure comprises a vacuum pump which lowers the overall pressure in the volume area of said another gas flow space, which is limited at least partially by the membrane and is located on the side of the membrane facing away from the breathing gas mixture to set the partial pressures of $N_2$, $CO_2$ and $H_2O$ by lowering the overall pressure on the side of the membrane facing away from the breathing gas mixture.

8. A process in accordance with claim 7, wherein the selectivity of the membrane for $CO_2$ relative to $N_2$ decreases in proportion to the partial pressure of $N_2$ on the flushing gas side and is maintained below 500.

9. A process in accordance with claim 5, wherein said means for reducing $CO_2$ partial pressure comprises a gas flushing means provided in communication with said another gas flow space for continuously moving flushing gas through said another gas flow space a vacuum pump which lowers the overall pressure in the volume area of said another gas flow space, which is limited at least partially by the membrane and is located on the side of the membrane facing away from the breathing gas mixture to set the partial pressures of $N_2$, $CO_2$ and $H_2O$ by the flushing gas and simultaneously lowering the overall pressure on the side of the membrane facing away from the breathing gas mixture.

10. A process in accordance with claim 1, wherein a relative humidity of at least 60% is set on at least one side of the membrane during the separation of $CO_2$ at the membrane.

11. A process in accordance with claim 10, wherein the relative humidity is set by at least one of expiratory breathing gases in the expired from the breathing gas mixture flow and by an additional humidification source.

12. A device for separating $CO_2$ from a breathing gas mixture, the device comprising:
a breathing gas device providing an expired breathing gas mixture flow;
a breathing gas mixture flow space through which the expired breathing gas mixture flows;
another gas flow space;
a separating element comprising a selective semipermeable membrane separating volume areas of said breathing gas mixture flow space and said another gas flow space on each side of said selective semipermeable membrane, said selective semipermeable membrane defining a breathing gas mixture guide on one side of said selective semipermeable membrane for forming a separating element, said selective semipermeable membrane comprising a porous polymer support structure and amine groups bound covalently to the polymer, through which transport of the components of the gas mixture can take place, said selective semipermeable membrane having a permeability for $CO_2$ that is substantially higher than the permeability for the other gas components of the breathing gas mixture, said selective semipermeable membrane guiding the gas mixture along the membrane to separate said volume areas on each side of said selective semipermeable membrane; and means for reducing $CO_2$ partial pressure in said another gas flow space such that a $CO_2$ partial pressure in said another gas flow space is below a $CO_2$ partial pressure prevailing in said breathing gas mixture flow space.

13. A device in accordance with claim 12, wherein the breathing gas mixture flow contains halogenated hydrocarbons and the selective semipermeable membrane is provided with a porous support structure, which is resistant to halogenated hydrocarbons and through which the transport of $CO_2$ takes place at a selectivity of at least 50 relative to the transport of halogenated hydrocarbons.

14. A device in accordance with claim 12, wherein a $CO_2$ partial pressure that is below 500 Pa prevails in said another gas flow space on a side of the membrane facing away from the breathing gas mixture.

15. A device in accordance with claim 12, wherein said means for reducing $CO_2$ partial pressure comprises a gas flushing means provided in communication with said another gas flow space for continuously moving flushing gas through said another gas flow space.

16. A device in accordance with claim 12, wherein said means for reducing $CO_2$ partial pressure comprises a vacuum pump which lowers the overall pressure in the volume area of said another gas flow space, which is limited at least partially by the membrane and is located on the side of the membrane facing away from the breathing gas mixture.

17. A device in accordance with claim 12, wherein said means for reducing $CO_2$ partial pressure comprises:
   a gas flushing means provided in communication with said another gas flow space for gas flushing of the side of the membrane facing away from the breathing gas mixture; and
   a vacuum pump which lowers the overall pressure in the volume area of said another gas flow space, which is limited at least partially by the membrane and is located on the side of the membrane facing away from the breathing gas mixture.

18. A device in accordance with claim 12, further comprising moistening means comprising a humidifier connected to the breathing gas device for humidifying the expired breathing gas mixture flow for moistening the membrane on the side of the breathing gas mixture.

19. A device in accordance with claim 12, further comprising moistening means for moistening the side of the membrane facing away from the breathing gas mixture.

20. A device in accordance with claim 12, wherein said membrane contains buffer substances, including one of trihydroxymethylaminomethane, borates or carbonates, which maintain the pH value above a value of 7.

21. A device in accordance with claim 12, wherein the breathing gas device is one of an anesthesia apparatus or respirator wherein said breathing gas mixture flows from said anesthesia apparatus or respirator.

22. A device in accordance with claim 12, wherein said separating element further comprises a support structure in the form of a counterflow hollow fiber membrane module supporting said selective semipermeable membrane.

23. A device in accordance with claim 12, wherein said separating element further comprises a support structure in the form of a counterflow flat membrane module supporting said selective semipermeable membrane.

24. A device in accordance with claim 12, wherein said separating element further comprises a support structure in the form of a cross-flow flat membrane module supporting said selective semipermeable membrane.

25. A device in accordance with claim 12, wherein said separating element further comprises a support structure in the form of a wound membrane module supporting said selective semipermeable membrane.

26. A device in accordance with claim 12, wherein said selective semipermeable membrane is formed of polyvinylamine and is connected to an asymmetrically porous hollow fiber membrane as a support structure or is applied to same, the membrane being arranged on the side of the small pore sizes of the support structure.

27. A device in accordance with claim 26, wherein the porous hollow fiber membrane consists of polysulfone, polyacrylonitrile, cellulose acetate or polyether sulfone.

28. A device in accordance with claim 12, wherein the separating element is equipped with a memory element, which can be read in a wireless manner, can be written to and is designed as a transponder and contains a model identification and/or operating parameters and/or characteristics of the element for identification and/or calculation of the state of consumption or the remaining use time of the element, the calculation being carried out in a computing unit of an anesthesia apparatus or a respirator.

* * * * *